(12) United States Patent
Weinberg et al.

(10) Patent No.: US 9,212,347 B2
(45) Date of Patent: Dec. 15, 2015

(54) PROGENITOR CELLS AND USES THEREOF

(75) Inventors: Robert A. Weinberg, Brookline, MA (US); Sendurai A. Mani, Houston, TX (US); Mai-Jing Liao, Winchester, MA (US)

(73) Assignee: WHITEHEAD INSTITUTE, Cambridge, MA (US)

( * ) Notice: Subject to any disclaimer, the term of this patent is extended or adjusted under 35 U.S.C. 154(b) by 0 days.

(21) Appl. No.: 13/526,271

(22) Filed: Jun. 18, 2012

(65) Prior Publication Data
US 2012/0258084 A1   Oct. 11, 2012

Related U.S. Application Data

(63) Continuation of application No. 11/922,911, filed as application No. PCT/US2006/025589 on Jun. 30, 2006, now abandoned.

(60) Provisional application No. 60/696,438, filed on Jun. 30, 2005.

(51) Int. Cl.
C12N 5/071 (2010.01)
C12N 5/10 (2006.01)

(52) U.S. Cl.
CPC .......... *C12N 5/0631* (2013.01); *C12N 2501/15* (2013.01); *C12N 2501/60* (2013.01); *C12N 2510/00* (2013.01)

(58) Field of Classification Search
None
See application file for complete search history.

(56) References Cited

U.S. PATENT DOCUMENTS 6,326,201 B1 * 12/2001 Fung et al. ............... 435/377

FOREIGN PATENT DOCUMENTS

| WO | WO 02/12447    | 2/2002 |
| WO | WO 03/050502 A | 6/2003 |
| WO | WO 2005/005601 A | 1/2005 |

OTHER PUBLICATIONS

Boehmelt et al. Hormone-regulated v-rel estrogen receptor fusion protein: reversible induction of cell transformation and cellular gene expression. The EMBO Journal vol. 1 1 No. 12 pp. 4641-4652, 1992.*
Eilers et al. Chimaeras of Myc oncoprotein and steroid receptors cause hormone-dependent transformation of cells. Nature . vol. 340. 1989. p. 66-68.*
Yang et al. Twist, a Master Regulator of Morphogenesis, Plays an Essential Role in Tumor Metastasis. Cell, vol. 117, 927-939, Jun. 25, 2004.*
Zavadil et al. Genetic programs of epithelial cell plasticity directed by transforming growth factor-b. PNAS. Jun. 5, 2001. vol. 98: No. 12. p. 6686-6691.*
Zavadil et al. Integration of TGF-b/Smad and Jagged1/Notch signalling in epithelial-to-mesenchymal transition. The EMBO Journal (2004) 23, 1155-1165.*
Atouf F, Park CH, Pechhold K, et al. No evidence for mouse pancreatic beta-cell epithelial-mesenchymal transition in vitro. Diabetes. 2007;56:699-702.
Morton RA Russell A. Morton, Elizabeth Geras-Raaka, Leah M. Wilson, Bruce M. Raaka, and Marvin C. Gershengorn. Endocrine precursor cells from mouse islets are not generated by epithelial-to-mesenchymal transition of mature beta cells. Mol Cell Endocrinol. 2007;270:87-93.
Gershengorn Marvin C et al: "Epithelial-to-mesenchymal transition generates proliferative human iselt precursor cells" Science, Washington, DC, vol. 306, bo. 5705, Dec. 24, 2004, pp. 2261-2264, XP002434842 ISSN: 0036-8075.
Cano A et al: The Transcription Factor Snails Controls Epithelial-Mesenchymal Transitions by Repressing E-Cadherin Expression Nature Cell Biology, MacMillan Publishers, GB, vol. 2, Feb. 1, 2000 pp. 76-83, XP002941264 ISSN: 1465-7392.
Mani A et al: "Mesenchyme forkhead 1 (FOXC2) is a marker for basal like breast cancer and involved in inducing metastasis and EMT" Clinical & Experimental Metastasis, vol. 21, No. 7, 2004, p. 654, XP002487547 & 10$^{th}$ International Congress of the Metastasis-Research-Society; Genoa, Italy; Sep. 17-20, 2004 ISSN: 0262-0898.
Moustakas Aritidis et al: "Mechanisms of TGF-beta signaling in regulation of cell growth and differentiation" Immunology Letters, vol. 82, No. 1-2, Jun. 3, 2002, pp. 85-91, XP002487548 ISSN: 0165-2478.
Mani A et al: "The epithelial-mesenchymal transition generates cells with properties of stem cells" Cek=II May 16, 2008, vol. 133, No. 4, May 16, 2008, pp. 704-715, XP 002487549 ISSN: 1097-4172.
JP Office Action Mailing Date Oct. 16, 2012.
Gershengorn MC, Geras-Raaka E, Hardikar AA, et al. Are better islet cell precursors generated by epithelial-to-mesenchymal transition? Cell Cycle. 2005;4:380-382.
Ouziel-Yahalom L, Zalzman M, Anker-Kitai L, et al. Expansion and redifferentiation of adult human pancreatic islet cells. Biochem Biophys Res Commun. 2006;341:291-298.
Xiao T et al. Structural basis for allostery in integrins and binding to fibrinogen-mimetic therapeutics. Nature. Nov. 4, 2004;432(7013):59-67. Epub Sep. 19, 2004.
Chase LG, Ulloa-Montoya F, Kidder BL, et al. Islet-derived fibroblast-like cells are not derived via epithelial-mesenchymal transition from Pdx-1 or insulin-positive cells. Diabetes. 2007;56:3-7.
Al-Hajj M et al. Prospective identification of tumorigenic breast cancer cells. Proc Natl Acad Sci U S A. Apr. 1, 2003;100(7):3983-8. Epub Mar. 10, 2003. Erratum in: Proc Natl Acad Sci U S A. May 27, 2003;100(11):6890.
Weinberg N, Ouziel-Yahalom L, Knoller S, et al. Lineage tracing evidence for in vitro dedifferentiation but rare proliferation of mouse pancreatic beta-cells. Diabetes. 2007;56:1299-1304.

(Continued)

*Primary Examiner* — Tae Yoon Kim
(74) *Attorney, Agent, or Firm* — Mark S. Cohen; Pearl Cohen Zedek Latzer Baratz LLP

(57) ABSTRACT

Methods for preparing progenitor cells are described where epithelial cells are induced to undergo epithelial-mesenchymal transition as a result of exposure to an inducing agent or introduction of a gene therein that induces epithelial-mesenchymal transition. Progenitor cells resulting therefrom have use in cell-based therapies, among other utilities.

27 Claims, 8 Drawing Sheets

(56) References Cited

OTHER PUBLICATIONS

Davani B et al. Human islet-derived precursor cells are mesenchymal stromal cells that differentiate and mature to hormone-expressing cells in vivo.,Stem Cells. Dec. 2007;25(12):3215-22. Epub Sep. 27, 2007.
Choi Y et al, Adult pancreas generates multipotent stem cells and pancreatic and nonpancreatic progeny. Stem Cells. 2004;22(6):1070-84.
European Search Report Mailing Date Aug. 4, 2008.
PCT Search Report Mailing Date Apr. 3, 2007.
Kasai H et al., TGF-beta1 induces human alveolar epithelial to mesenchymal cell transition (EMT). Respir Res. Jun. 9, 2005;6:56.
Saika S et al. Smad3 is required for dedifferentiation of retinal pigment epithelium following retinal detachment in mice. Lab Invest. Oct. 2004;84(10):1245-58.
Savagner P et al., The zinc-finger protein slug causes desmosome dissociation, an initial and necessary step for growth factor-induced epithelial-mesenchymal transition. J Cell Biol. Jun. 16, 1997;137(6):1403-19.
Valcourt U et al. TGF-beta and the Smad signaling pathway support transcriptomic reprogramming during epithelial-mesenchymal cell transition. Mol Biol Cell. Apr. 2005;16(4):1987-2002. Epub Feb. 2, 2005.
Willis BC et al. Induction of epithelial-mesenchymal transition in alveolar epithelial cells by transforming growth factor-beta1: potential role in idiopathic pulmonary fibrosis. Am J Pathol. May 2005;166(5):1321-32.
Holger A Russ et al. "In Vitro Proliferation of Cells Derived From Adult Human β-Cells Revealed by Cell-Lineage Tracing" Diabetes, vol. 57, Jun. 2008.
Holger A. Russ et al. "Epithelial-Mesenchymal Transition in Cells Expanded In Vitro from Lineage-Traced Adult Human Pancreatic Beta Cells" PLoS One www.plosone.org. Jul. 2009, vol. 4, Issue 7, e6417.
Seeberger K et al. "Epithelial Cells Within the Human Pancreas do not Coexpress Mesenchymal antigens: Epithelial-Mesenchymal Transition is an Artifact of Cell Culture" Laboratory Invetigatation (2009) 89, 110-121.
Chase L. et al "Islet-Derived Fibroblast-Like Cells Are Not Derived via Epithelial-Mesenchymal Transition From Pdx-1 or Insulin-Positive Cells" Rapid Publications Diabetes 2007 V 56 N1 pp. 3-7.

* cited by examiner

A

B

A

B

PROGENITOR CELLS AND USES THEREOF

CROSS REFERENCE TO RELATED APPLICATIONS

This application is a continuation of U.S. application Ser. No. 11/922,911, filed 27 Apr. 2009 now abandoned, claiming priority of PCT International Application No. PCT/US2006/025589, International Filing Date 30 Jun. 2006, claiming priority of U.S. Provisional Patent Application 60/696,438, filed 30 Jun. 2005, all of which are incorporated herein by reference in their entireties.

GOVERNMENT INTEREST STATEMENT

This invention was made in whole or in part with government support under Grant Numbers P01 CA80111-06 1602 (National Cancer Institute) and 1F32CA101507-01, awarded by the National Institute of Health. The government may have certain rights in the invention.

BACKGROUND OF THE INVENTION

Significant potential for the treatment of numerous diseases and conditions is offered through the use of progenitor cells and cell-based therapies. Perhaps the most important potential application of human progenitor cells is the generation of differentiated cells and tissues either in vitro or in situ that could be used for cell-based therapies. Today, donated organs and tissues are often used to replace ailing or destroyed tissue, but the need for transplantable tissues and organs far outweighs the available supply. Progenitor cells, directed to differentiate into specific cell types, offer the possibility of a renewable source of replacement cells and tissues to treat numerous diseases including Parkinson's and Alzheimer's diseases, spinal cord injury, stroke, burns, heart disease, diabetes, osteoarthritis, and rheumatoid arthritis, to name only a few examples.

Preliminary research in mice and other animals indicates that bone marrow stem cells, transplanted into a damaged heart, can generate heart muscle cells and successfully repopulate the heart tissue. Other recent studies in cell culture systems indicate that it may be possible to direct the differentiation of embryonic stem cells or adult bone marrow cells into heart muscle cells.

Scientists in many laboratories are trying to find ways to grow adult stem cells in cell culture and manipulate them to generate specific cell types so they can be used to treat injury or disease. Some examples of potential treatments include replacing the dopamine-producing cells in the brains of Parkinson's patients, developing insulin-producing cells for type I diabetes and repairing damaged heart muscle following a heart attack with cardiac muscle cells.

While the utility of stem or progenitor cells holds significant promise in the future of medicine, obtaining sufficient quantities of undifferentiated progenitor cells and maintaining them in an undifferentiated state has been a challenge to biomedical research, as has been controlling the differentiation of progenitor cells in situ into desirable terminal cell types.

During embryogenesis, epithelial cells undergo a change in phenotype into a non-fibroblastic, mesenchymal-type cell in a process called epithelial-mesenchymal transition (EMT). Mesenchymal cells generated during embryogenesis by EMT then give rise to the mesodermal cell types in the embryo, such as skeletal bone, connective tissue of the skin, reproductive organs, cardiac muscle, skeletal muscle, megakaryocytes (red blood cell precursors) and smooth muscle cells. For the purposes of this application, an EMT thereby includes processes wherein epithelial cells undergo either partial or complete change into mesenchymal cells. Associated with this transition is a change in markers characteristic of EMT.

SUMMARY OF THE INVENTION

In one embodiment, the invention is directed to methods for generating populations of progenitor cells. In one embodiment, a method for generating progenitor cells from epithelial cells is provided that includes the steps of (a) obtaining a population of epithelial cells, and (b) inducing epithelial-mesenchymal transition in the population of epithelial cells, whereby progenitor cells are generated in the population. In another embodiment, progenitor cells are isolated from the population following step (b). In another embodiment, the population of epithelial cells is exposed to an agent that induces epithelial-mesenchymal transition. In yet another embodiment, inducing epithelial-mesenchymal transition results from introducing into the population of epithelial cells a gene the expression of which induces epithelial-mesenchymal transition. In still yet another embodiment, inducing epithelial-mesenchymal transition is achieved by first introducing into the epithelial cells an inducible gene that on induction results in epithelial-mesenchymal transition, and exposing the cells to an inducer of the inducible gene.

In a further embodiment of the invention, progenitor cells, prepared as described above comprising an inducible epithelial-mesenchymal transition gene and exposed to the inducer, can be induced to differentiate by withdrawing the inducer. Progenitor cells prepared as described above can be propagated in culture in the presence of the inducer, then used for cell-based therapies. In another embodiment, this method can be used, for example, to induce the differentiation of progenitor cells at a target site in vivo by preparing progenitor cells as described and administering them to a subject or to a target site in the subject, where in the absence of the inducer the cells differentiate. In another embodiment, this method can be carried out by the steps of (a) generating progenitor cells comprising an inducible epithelial-mesenchymal transition gene as described above, (b) introducing the progenitor cells in vivo and administering the inducer in vivo such that the progenitor cells are maintained in an undifferentiated state; (c) waiting a sufficient period of time for the progenitor cells to populate a target site in vivo; and then (d) discontinuing administration of the inducer.

The invention is not limited by the type of or origin of the epithelial cells. Primary epithelial cells can be obtained from a human or other mammalian subject who may be in the intended recipient of cell-based therapy based on the present invention, or obtained from discarded surgical or cellular samples from a subject, or from a propagated cell line.

The progenitor cells generated by the methods described herein exhibit a cell surface marker expression pattern characteristic of progenitor cells such as $CD44^{high}$ and $CD24^{low}$. They may also express progenitor cell marker $CD10^{pos}$. The progenitor cells also exhibit at least one marker of epithelial-mesenchymal transition, from among $FOXC2^{pos}$, N-cadherin$^{high}$, E-cadherin$^{low/neg}$, alpha-catenin$^{low/neg}$, gamma-catenin$^{low/neg}$, vimentin$^{pos}$, or fibronectin$^{pos}$. Moreover, the progenitor cells of the invention have multi-lineage potential.

In another embodiment, the invention is directed to progenitor cells that are prepared by (a) obtaining a population of epithelial cells, and (b) inducing epithelial-mesenchymal transition in the population of epithelial cells. Optionally, the progenitor cells can be isolated from the population. Inducing epithelial-mesenchymal transition can be carried out by any of several methods such as those described above.

In another embodiment of the invention, modified epithelial cells are provided that include at least one inducible gene that results in epithelial-mesenchymal transition when the cells are exposed to an inducer.

In yet another embodiment, the invention is directed to modified progenitor cells that contain a vector comprising at least one epithelial-mesenchymal transition gene under the control of a constitutive promoter. In one embodiment, the cells are isolated.

In still yet a further embodiment of the invention, various uses of the progenitor cells of the invention are provided. Cell-based therapy to a mammalian subject can be achieved by transplanting progenitor cells of the invention into the subject. In one embodiment, progenitor cells of the invention are administered to a mammalian subject to provide therapeutic benefit, for example in the treatment of one of the diseases mentioned herein, such as Parkinson's disease, Alzheimer's diseases, spinal cord injury, stroke, burns, heart disease, diabetes, osteoarthritis, and rheumatoid arthritis. In another embodiment herein, progenitor cells containing at least an inducible gene that results in epithelial-mesenchymal transition when exposed to inducer are administered to a subject in need of therapy. In another embodiment, such progenitor cells are administered along with an inducer. After waiting a sufficient period of time for the progenitor cells to populate at least one target site, administration of the inducer is discontinued. The progenitor cells can be administered into the circulation or into a target site. Progenitor cells of the invention can also be used to grow replacement tissues ex vivo or in vitro, for subsequent transplantation or implantation into a subject in need thereof In another embodiment, progenitor cells are genetically modified prior to administration.

In another embodiment, a new progenitor cell marker, FOXC2, is identified that is useful for many purposes, such as but not limited to identifying progenitor cells in a cellular population, tissue, or organ for the purpose of conducting cell-based therapies, identifying agents and conditions that induce the formation and maintenance of a progenitor cell phenotype, immunohistochemistry, to name just a few.

These and other embodiments of the invention will be evident from the following description of the drawings and ensuing detailed description of the invention.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE PRESENT INVENTION

Figure 1:
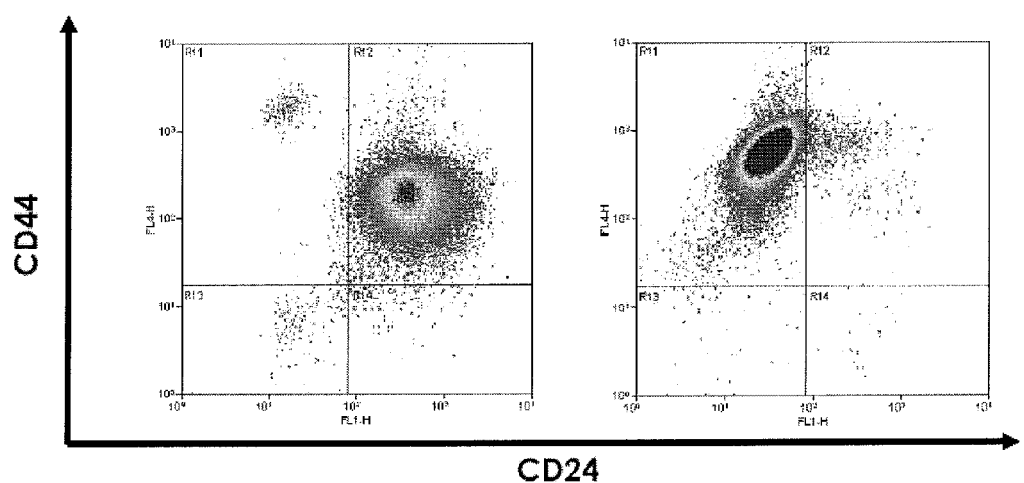
FIG. 1 shows that induction of epithelial-mesenchymal transition in mouse mammary epithelial cells by exposure to TGF-β1 for 12 days results in a population of cells with characteristics of progenitor cells, exhibiting a marker pattern of $CD44^{high}$ and $CD24^{low}$.
Figure 1:
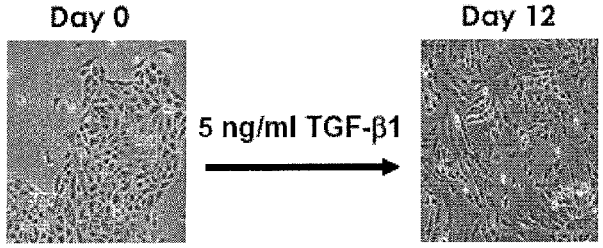

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Readily and facilely generatable sources of progenitor cells are a key factor in translating the potential of cell-based therapies into demonstrable clinical benefit. As used herein, the term progenitor cell is synonymous with stem cell and refers to undifferentiated cells with multi-lineage potential that, among other characteristics, can give rise to various cell types. For the purposes of the present application, a progenitor cell is defined as a cell that is (a) relatively undifferentiated; (b) capable of generating daughter cells ("daughters") that are similarly undifferentiated; (c) capable of generating a lineage of such daughters that are able to reproduce themselves through a large number of successive growth-and-division cycles; (d)capable of generating daughters that are able, under appropriate conditions, to enter into a program of differentiation that enables such cells to acquire the specialized traits of one or another functional tissue in the mammalian body. In one embodiment, a subpopulation of cells exhibiting characteristics of having undergone epithelial-mesenchymal transition (EMT), an embryonic developmental process, has been identified in vivo, and importantly, such cells unexpectedly also exhibit typical progenitor cell characteristics. In another embodiment, permanently or transiently inducing EMT by various methods and identifying progenitor cell properties therein, thus provides a facile means for generating useful quantities of progenitor cells. Moreover, control over the transience of the EMT phenotype and thus the progenitor phenotype permits therapeutically-directed differentiation of progenitor cells into terminal cell types.

Thus, in one embodiment, useful populations of progenitor cells can be generated by inducing epithelial cells to undergo epithelial-mesenchymal transition, yielding attendant populations of progenitor cells useful in a myriad of applications such as transplant for cell-based therapeutics, screening compounds for biological activities and manufacturing of biologics, to name just a few.

Progenitor cells embodied herein can differentiate into terminal cell types in situ. Furthermore, progenitor cells of the invention derived from mammary epithelial cells will form mammospheres in vitro. Inclusion of differentiation factors will induce the formation of particular cell types. Cells that do not show EMT characteristics, such as having a marker expression of $CD44^{low}$ and $CD24^{high}$, will not form a ductal tree nor mammospheres.

Also as shown herein, in the case of epithelial cells exposed to agents that induce EMT and generate a population of progenitor cells, and those epithelial cells containing an inducible EMT gene and exposed to the inducer, such progenitor cells of the present invention will differentiate under the appropriate conditions or revert to an epithelial phenotype, when no longer exposed to the agent that induced EMT or when no longer exposed to the inducer. In either case, such cells can be used for the various cell-based therapies described herein by example only, and for all of the uses of progenitor cells described in the art. The examples provided herein are merely exemplary and non-limiting of such uses.

The invention described herein is applicable to cells from any mammalian source, typically human, but domesticated, livestock and zoo animals are also embraced herein. Patients who may benefit from stem cell transplants or other cell-based therapies based on the invention are typically humans but this is not so limiting and other mammalian species may be recipients as well.

There are numerous uses of progenitor cells that are prepared as described herein. Such uses include cell-based therapies in which progenitor cells are transplanted or implanted into a subject, methods for evaluating or screening biological activity of a therapeutic or biologically-active molecule in progenitor cells, methods for identifying improved procedures for growing, maintaining and differentiating progenitor cells, and for production including manufacturing of progenitor cell-derived products such as recombinant proteins, peptides, fusion polypeptides, to name just a few.

Cell-based therapies using progenitor cells include the treatment of such diseases as Parkinson's disease, Alzheimer's disease, spinal cord injury, stroke, burns, heart disease, diabetes, osteoarthritis, and rheumatoid arthritis. Moreover, cardiovascular, bone, muscle, and brain are among the cells and tissues toward which progenitor cell-based therapies can be directed.

Methods for evaluating or screening biological activities of therapeutic or biologically-active molecules includes high-throughput screening to identify new lead compounds, as well as identifying agents and conditions that favor the differentiation of progenitor cells into particular cell lineages, are examples of other uses of the progenitor cells of the invention.

Methods using the progenitor cells of the invention for identifying improved procedures for growing, maintaining and differentiating progenitor cells are yet other uses of the invention. Agents and conditions that favor or induce differentiation of progenitor cells into particular terminal cell types can be readily undertaken in screening procedures utilizing the progenitor cells of the invention, for example, by identifying changes in markers or secreted proteins indicative of differentiation.

Utility of the progenitor cells of the invention is also evident in production of biologically and therapeutically useful biomolecules such as nucleic acids and proteins. Maintaining progenitor cells in a continuously proliferating stem state can take advantage of the expression and secretion of an endogenous gene product or that of an inserted gene via a vector comprising a constitutive or inducible promoter to produce quantities of material from human (or other species) cells, providing a cost effective and regulatorily facile manufacturing process. Such a process can generate recombinant proteins, peptides, fusion polypeptides, nucleic acids, and any other useful cellular product.

Thus, as described above, one embodiment the invention is directed to methods for generating populations of progenitor cells by carrying out at least the steps of (a) obtaining a population of epithelial cells, and (b) inducing epithelial-mesenchymal transition in the population of epithelial cells, whereby progenitor cells are generated in the population. Optionally, in another embodiment, the progenitor cells present in the population after step (b) can be isolated. In another embodiment, inducing epithelial-mesenchymal transition comprises exposing the population of epithelial cells to an agent that induces epithelial-mesenchymal transition, such as but not limited to TGF-β1, FGF-1, EGF, HGF/SF, BFGF, and PDGF. In another embodiment, inducing epithelial-mesenchymal transition is achieved by introducing into the population of epithelial cells a gene, such as may be present on a vector under the control of a constitutive promoter, wherein expression of the gene induces epithelial-mesenchymal transition. Non-limiting examples of suitable genes include transcription factors. Examples of suitable transcription factor genes include Snail, Twist, Slug, SIP1, FOXC1, FOXC2, Goosecoid, E47 or a functional variant of any of the foregoing.

Methods for introducing vectors and other nucleic acids are well known to those skilled in the art, and may include, in some embodiments, the use of lipid or liposome based delivery (WO 96/18372; WO 93/24640; Mannino and Gould-Fogerite (1988) BioTechniques 6(7): 682-691; Rose U.S. Pat. No. 5,279,833; WO 91/06309; and Feigner et al. (1987) Proc. Natl. Acad. Sci. USA 84: 7413-7414) or the use of replication-defective retroviral vectors comprising a nucleic acid sequence as described (see, e.g., Miller et al. (1990) Mol. Cell. Biol. 10:4239 (1990); Kolberg (1992) J. NIH Res. 4: 43, and Cometta et al. (1991) Hum. Gene Ther. 2: 215) Anderson, Science (1992) 256: 808-813; Nabel and Feigner (1993) TIBTECH 11: 211-217; Mitani and Caskey (1993) TIBTECH 11: 162-166; Mulligan (1993) Science, 926-932; Dillon (1993) TIBTECH 11: 167-175; Miller (1992) Nature 357: 455-460; Van Brunt (1988) Biotechnology 6(10): 11491154; Vigne (1995) Restorative Neurology and Neuroscience 8: 35-36; Kremer and Perricaudet (1995) British Medical Bulletin 51(1) 31-44; Haddada et al. (1995) in Current Topics in Microbiology and Immunology, Doerfler and Bohm (eds) Springer-Verlag, Heidelberg Germany; and Yu et al., (1994) Gene Therapy, 1: 13-26. In one embodiment, the method described by Elenbaas et al., 2001, Human breast cancer cells generated by oncogenic transformation of primary mammary epithelial cells, Genes & Development 15:50-65, is used to introduce the Snail or Twist gene into an epithelial cell.

In yet another embodiment, inducing epithelial-mesenchymal transition can be achieved by first introducing into the epithelial cells an inducible EMT protein or gene encoding an inducible EMT protein, then exposing the cells to the inducer. Preparation and introduction of inducible EMT proteins and genes can be readily achieved following teachings in the art. For example, in one embodiment, an EMT gene can be provided on a vector that is under the control of an inducible promoter, wherein expression of the gene induces epithelial-mesenchymal transition, such that when the cells are exposed to the inducer, the expression of the gene transiently induces epithelial-mesenchymal transition. The inducible gene can include a member of any of the aforementioned genes, such as but not limited to transcription factor genes, functionally associated with an inducible promoter, such as the tetracycline responsive promoter. In another embodiment, as shown in the examples below, a gene encoding a fusion polypeptide comprising a transcription factor and the estrogen receptor can be prepared and introduced into cells. In the instance where the estrogen receptor is used, the inducer can be an estrogen receptor modulator such as tamoxifen or analog thereof In one embodiment, a modified estrogen receptor only responsive to tamoxifen or an analog thereof, but not to estrogen, is used. Expression of the fusion polypeptide provides a means for inducing EMT; exposure of the cells to the estrogen activates the transcription factor and induces EMT. Methods for preparing such inducible fusion polypeptides can be found in, for example, Eilers et al., 1989, Chimaeras of Myc oncoprotein and steroid receptors cause hormone-dependent transformation of cells, Nature 340:66-68.

In another embodiment, the invention embraces progenitor cells prepared as described with an inducible EMT protein or gene and exposed to an inducer, which can be induced to differentiate by withdrawing the inducer. In one embodiment, progenitor cells so prepared and propagated in the presence of the inducer to maintain the progenitor state can be administered to a subject; after administration, in the absence of the inducer, the progenitor cells differentiate. In another embodiment, to prolong the progenitor characteristics of the cells after administration or to induce the differentiation of the progenitor cells at a target site in vivo, the following methods can be carried out: (a) generating progenitor cells comprising an inducible EMT gene as described above, (b) introducing the progenitor cells in vivo and administering the inducer in vivo such that the progenitor cells are maintained in an undifferentiated state; (c) allowing the progenitor cells to populate a target site in vivo; and then (d) stopping the administration of the inducer.

As noted above, the invention is not limited by the type of or origin of the epithelial cells. Examples include epithelial cells from mammary tissue, prostate, lung, as well as keratinocytes. Epithelial cells useful in the embodiments herein include squamous epithelial cells, such as those found in the alveoli of the lungs, kidneys, and the major cavities of the body; cuboidal epithelial cells, columnar epithelial cells, such as those lining the small intestine; and transitional epithelial cells, such as those lining the bladder and ureter. Other sources include epithelial cells lining the ducts of submandibular glands. These sources are non-limiting and only exemplary of the variety of sources of epithelial cells in the various embodiments of the invention.

Epithelial cells can be obtained from a human or other mammalian subject who may be in the intended recipient of cell-based therapy based on the present invention, or obtained from discarded surgical or cellular samples from a subject, or from a propagated cell line. Genetic modification of the cells can be carried out, for example, by introducing or knocking out one or more genes, prior to therapeutic use, in order to, for example, alter the histocompatibility of allogeneic progenitor cells or correct a genetic defect in autologous cells. These examples are merely illustrative of an embodiment of the invention and are not intended to be limiting.

The progenitor cells generated by the methods described herein exhibit a cell surface marker expression pattern characteristic of progenitor cells such as $CD44^{high}$ and $CD24^{low}$. They may also express progenitor cell marker $CD10^{pos}$. The progenitor cells can also exhibit at least one marker of epithelial-mesenchymal transition, from among $FOXC2^{pos}$, $N\text{-cadherin}^{high}$, $\text{Ecadherin}^{low/neg}$, $\text{alpha-catenin}^{low/neg}$, $\text{gamma-catenin}^{low.neg}$, $\text{vimentin}^{pos}$, or $\text{fibronectin}^{pos}$. Expression of the levels of these markers can be measured, by way of non-limiting example, by quantitating levels of the aforementioned proteins in or on the cells, or by measurement of levels of mRNA. Moreover, the progenitor cells of the invention can have multi-lineage potential. The progenitor cells may be able to spawn multiple distinct types of differentiated descendants or, alternatively, have single-lineage potential, in which case they may be able to spawn descendants that are capable of differentiating into only a single cell type. Marker patterns of cells can be readily determined by techniques, such as cell fluorescence-activated cell sorting and immunohistochemistry to name some non-limiting examples.

Among those cell markers mentioned above, FOXC2 is newly identified herein as a progenitor cell marker that can be used to identify progenitor cells among a population of cells, or within a tissue or organ. FOXC2, an abbreviation for forkhead box C2, (MFH-1, mesenchyme forkhead 1), is a member of the Fork head transcription factor family It has a Locuslink access number 2303, a Refseq access number NM_005251, and a Unigene access number Hs.558329, and is also known as FKHL14, MFH-1 and MFH1. As will be seen in the examples below, expression of FOXC2 in epithelial cells is an indicator of progenitor cell characteristics, as is noted in endogenous populations of EMT cells from mammary reduction surgery samples, and epithelial cells induced to undergo EMT by introduction of an inducible or constitutive EMT gene.

Various binding reagents to FOXC2, such as antibodies, can be labeled with a detectable label and used to identify cells expressing this marker, for the various uses exemplified herein. FOXC2 mRNA levels are also useful for identifying cells with progenitor characteristics. Previously recognized as a cancer cell marker (see, for example, Katoh M, Katoh M., Human FOX gene family, Int J Oncol. 2004 November; 25(5):1495-500), in one embodiment herein FOXC2 is used among the various progenitor cell markers to identify epithelial cells that have undergone EMT and exhibit a progenitor cell phenotype.

Progenitor cells of the invention demonstrate progenitor cell phenotype in at least one assay. For example, in the use of mammary epithelial cells that have undergone EMT in accordance with the teachings herein, the resultant progenitor cells can form mammospheres in vitro, and can form ductal trees if implanted into mammary fat pads in vivo.

In another embodiment, the invention is directed to progenitor cells that are prepared by (a) obtaining a population of epithelial cells and (b) inducing epithelial-mesenchymal transition in the population of epithelial cells. In another embodiment, progenitor cells can be isolated from the population in step (b). As mentioned above, inducing can be carried out by any of several methods such as those described above. The progenitor cells generated by the process described herein exhibit expression of both progenitor and epithelial-mesenchymal transition markers as described herein.

In another embodiment, modified epithelial cells are provided that comprise an inducible gene wherein the epithelial cells will undergo epithelial-mesenchymal transition if the cells are exposed to an inducer. Such cells can comprise an inducible gene in the form of an introduced vector comprising at least one gene under the control of an inducible promoter, wherein the vector contains at least one gene that induces epithelial-mesenchymal transition. In another embodiment, the inducible gene can encode a polypeptide that comprises a transcription factor that becomes activated in the presence of the inducer, and the activated transcription factor induces EMT. The transcription factor gene can be any gene the expression of which induces EMT, such as but not limited to Snail, Twist, Slug, SIP1, FOXC1, FOXC2, Goosecoid, E47 or functional variant thereof. The promoter can be any inducible promoter. Such inventive cells exhibit an epithelial cell phenotype, but when exposed to the inducer, the epithelial cells undergo EMT and exhibit at least one cell marker of EMT as described hereinabove. Furthermore, upon exposure to the inducer, the modified epithelial cells have multi-lineage potential, and demonstrate progenitor cell phenotype in at least one assay.

In yet another embodiment, the invention is directed to progenitor cells that contain a vector comprising at least one gene under the control of a constitutive promoter. In one embodiment, the cells are isolated. Non-limiting examples of suitable genes include thoe encoding transcription factors. Examples of suitable transcription factor genes include Snail, Twist, Slug, SIP1 (Smad-interacting protein 1), FOXC1, FOXC2, Goosecoid, and E47 or a functional variant of any of the foregoing. A functional variant of any of the aforementioned genes includes sequence or other variations in the gene that retain the function of the gene, i.e., to induce epithelial-mesenchymal transition. Such transcription factors are known in the art as described, for example, in Elloul S et al., 2005, Snail, Slug, and Smad-interacting protein 1 as novel parameters of disease aggressiveness in metastatic ovarian and breast carcinoma, Cancer 103:1631-43).

In still yet a further embodiment of the invention, various uses of the progenitor cells of the invention are provided, not limited to the following merely illustrative examples. Cell-based therapy to a mammalian subject can be achieved by transplanting progenitor cells of the invention into the subject. In one embodiment, progenitor cells of the invention are administered to a mammalian subject to provide therapeutic benefit, for example in the treatment of one of the diseases mentioned herein, such as Parkinson's and Alzheimer's diseases, spinal cord injury, stroke, burns, heart disease, diabetes, osteoarthritis, and rheumatoid arthritis. As noted above, the multipotency of the progenitor cells of the invention can result in the differentiation into many tissue types, not limited to, for example, vascular, neuronal, heart and liver cells and tissues. In another embodiment herein, progenitor cells containing at least an inducible gene that induces epithelial-mesenchymal transition when exposed to inducer are administered to a subject in need of therapy. In another embodiment, such progenitor cells are administered to the subject along with an inducer. After waiting for the progenitor cells to populate at least one target site, administration of the inducer is discontinued, whereby the progenitor cells differentiate into therapeutically desirable cell types. The progenitor cells can be administered into the circulation or into a target site. In another embodiment, a differentiated cell type is administered to a patient who was suffering from the absence or loss of such cell type or, alternatively, if the introduced progenitor cell were genetically modified prior to being introduced into a patient, to provide said patient with a gene product that such patient was unable to make on his or her own. Progenitor cells of the invention can also be used to grow replacement tissues in vivo, ex vivo or in vitro, the latter for subsequent transplantation or implantation into a subject in need thereof In the use of the progenitor cells of the invention for cell-based therapies, progenitor cells prepared in accordance with the invention can be administered to a subject in need thereof by parenteral administration into the circulation or into an organ or tissue desirably populated by the progenitor cells. Cells can be administered in a pharmaceutically-acceptable diluent, carrier or excipient that permits delivery of the live cells to the desired site. Parenteral administration includes, by way of non-limiting examples, the intravenous, intraarterial, intradermal, intrathecal, intracranial, subcutaneous, and intraperitoneal routes.

The various steps by which the methods of the invention can be carried out and the progenitor cells generated thereby are described in the following sections. The description below is focused on human cells but the invention is not so limiting and every example has its applicability to the variety of non-human mammals to which the uses described herein would inure. While examples are given, these particular details are not to be construed as the only means by which the invention may be practiced, and one of ordinary skill will readily identify other means by which the same intentions can be achieved within the spirit of the invention.

1. Obtaining a Population of Epithelial Cells.

Epithelial cells useful in the practice of the invention can be obtained from any number of sources. Non-limiting examples of such sources include cell lines, autologous cells or tissue from a subject who will benefit from administration of progenitor cells derived therefrom, or allogeneic cells, i.e., cells from another individual that will be made into progenitor cells in accordance to the teachings herein then administered to a different individual.

Cell lines suitable as starting cells for the practice of the invention include non-transformed epithelial cells such as those described by and using the methods of Karsten et al., 1993, Subtypes of non-transformed human mammary epithelial cells cultured in vitro: histo-blood group antigen H type 2 defines basal cell-derived cells, Differentiation 54:55-66.

Typically, a patient or subject in need of cell-based therapy is the source of the epithelial cells of the invention. Epithelial cells can be easily isolated from cells harvested or tissue obtained surgically from patients, and the epithelial cells used in the practice of the invention. Among other sources, mammary tissue is a productive source of epithelial cells.

Allogeneic sources of progenitor cells for treatment or administration to a patient or subject are also included herein. A donor who is a family member, spouse, friend, or even a stranger, may contribute tissue containing epithelial cells. A patients undergoing a procedure that provides tissues containing epithelial cells, such as breast reduction surgery, is a source of allogeneic epithelial cells useful herein. Depending on the histocompatibility of the progenitor cells and the recipient, a recipient of allogeneic cells may require immunosuppression. In one embodiment described below, genetic modification of the progenitor cells is provided to address incompatibility.

In another embodiment, the present invention encompasses modifications of the cells that reduce or eliminate organ graft rejection when employing non-autologous cells or cell lines derived from the progenitor cells of the present invention. Methods known in the art can be used to alter the HLA type of the cells. Elimination or reduction of MHC class I molecules is accomplished by targeted knockout of the human $3_2$-microglobulin gene, as has been accomplished with mouse ES cells (Zijlstra et al, Nature 342:435-438, 1989). The presence of MHC class II glycoproteins may be reduced or eliminated by targeted knockout of the HLA-DP, -DQ, and -DR loci, which are analogous to knockouts of the E and A loci in mouse ES cells (Cosgrove et al, Cell 66:1051-1066, 1991).

Cultivation of epithelial cells from the aforementioned sources, as well as progenitor cells generated therefrom in accordance with the teaching herein, can be carried out by cultivation methods such as described in Dontu et al., 2003, In vitro propagation and transcriptional profiling of human mammary stem/progenitor cells, Genes Dev. 17:1253-70.

2. Inducing Epithelial-Mesenchymal Transition (EMT)

Induction of EMT to generate progenitor cells of the invention can be carried out in any number of ways without deviating from the spirit of the invention. One embodiment comprises exposing the population of epithelial cells to a molecule or agent that causes or induces epithelial-mesenchymal transition. In another embodiment, inducing epithelial-mesenchymal transition is achieved by introducing into the population of epithelial cells at least one gene whose expression induces epithelial-mesenchymal transition. In yet another embodiment, inducing epithelial-mesenchymal transition can be achieved by first introducing into the cells a protein or gene encoding a protein comprising inducible EMT gene, such that when the cells are exposed to an inducer, epithelial-mesenchymal transition is transiently induced; then exposing the cells to the inducer to effect the transition. This embodiment, as will be expanded on below, permits control over maintaining the EMT cells in a progenitor cell state for a pre-determined duration of time or until desired distribution of cells has occurred, and then by withdrawing the inducer results differentiation of the progenitor cells.

Exposure of various molecules or agents to epithelial cells can be used to induce EMT in a population of epithelial cells obtained as described above. Non-limiting examples of protein agents such as growth factors include transforming growth factor β1 (TGF-β1), fibroblast growth factor-1 (FGF-1), epidermal growth factor (EGF), hepatocyte growth factor/scatter factor (HGF/SF), basic fibroblast growth factor (BFGF), and platelet-derived growth factor (PDGF). These factors are well-known in the art and are available commercially from many suppliers, or can be prepared in the laboratory. In vitro, an appropriate concentration of the agent can be added to the culture medium and the cells incubated therein for a sufficient duration to induce EMT, after which time the presence of the inducer in the medium may optionally be removed. In one non-limiting example, 5 ng/ml TGF-β1 is used to induce EMT in mammary epithelial cells. The foregoing examples and conditions are merely illustrative of such methods of inducing EMT and other means for achieving the same results will be readily apparent.

In another embodiment, inducing epithelial-mesenchymal transition is achieved by introducing into the population of epithelial cells obtained as described above at least one gene that induces epithelial-mesenchymal transition. Such a gene typically will be that of a transcription factor, but the invention is not so limiting. Examples of suitable transcription factor genes include Snail, Twist, Slug, and SIP1, FOXC1, FOXC2, Goosecoid, E47 or a functional variant of any of the foregoing. Such modified epithelial cells are embodied within the invention.

The selected at least one gene can be provided on a vector that is under the control of a constitutive promoter. Constitutive promoters are known in the art and examples include simian virus promoters, herpes simplex virus promoters, papilloma virus promoters, adenovirus promoters, human immunodeficiency virus (HIV) promoters, Rous sarcoma virus promoters, cytomegalovirus (CMV) promoters, the long terminal repeats (LTRs) of Moloney murine leukemia virus and other retroviruses, the thymidine kinase promoter of herpes simplex virus as well as other viral promoters known to those of ordinary skill in the art. Preparation of a vector comprising the promoter and EMT inducing gene of interest is readily performed by guidance from the literature.

As will be further described below, at least one additional gene may be included in the vector in order to provide a means for identifying progenitor cells for isolation purposes.

Systems for linking control elements to coding sequences are well known in the art (general molecular biological and recombinant DNA techniques are described in Sambrook, Fritsch, and Maniatis, Molecular Cloning: A Laboratory Manual, Second Edition, Cold Spring Harbor Laboratory Press, Cold Spring Harbor, N.Y., 1989, which is incorporated herein by reference). Commercial vectors suitable for inserting coding sequence for expression in various mammalian cells under a variety of growth and induction conditions are also well known in the art. Non-limiting representative examples of suitable vectors for expression of polypeptides or proteins in mammalian cells include pcDNA1; pCD, see Okayama, et al. (1985) Mol. Cell Biol. 5:1136-1142; pMClneo Poly-A, see Thomas, et al. (1987) Cell 51:503-512; and a baculovirus vector such as pAC 373 or pAC 610. By way of non-limiting example, the methods described by Elenbaas et al., 2001, Genes & Development 15:50-65 can be followed utilizing the transcription factors mentioned herein in order to achieved one embodiment of the invention.

In yet another embodiment, transiently inducing epithelial-mesenchymal transition in epithelial cells can be achieved by first introducing into the epithelial cells an inducible gene that causes cells to undergo EMT, then exposing the cells to the inducer. Various methods are readily available to modify epithelial cells in this embodiment of the invention. In one embodiment, a vector is introduced into the epithelial cells, the vector comprising a gene that upon expression induces EMT, the gene being under the control of an inducible promoter. Subsequent to introducing the vector into the epithelial cells, the cells are exposed to the inducer of the promoter, in order to induce EMT. In another embodiment, a gene encoding a fusion polypeptide comprising an inducible EMT factor can be prepared. In one non-limiting example, a fusion polypeptide can comprise the estrogen receptor and the transcription factor Snail. Only upon exposure of the fusion polypeptide to a ligand of the estrogen receptor will the transcription factor be active. In one embodiment, a modified estrogen receptor only responsive to tamoxifen or an analog thereof, but not to estrogen, is used.

The inducible gene construct can include a member of any of the aforementioned genes that induce EMT, such as the transcription factors Snail and Slug. With regard to the inducible promoter, many are available and selection will be based on suitability for the desired utility of the progenitor cells generated thereby. For example, the inducible promoter can be a tetracycline responsive promoter, hormone-inducible promoters, radiation-inducible promoters, such as those employing the Egr-1 promoter or NF-kappaB promoter, or heat-inducible promoters. Suitable inducible promoters include, for example, the tetracycline responsive element (TRE) (See Gossen et al., Proc. Natl. Acad. Sci. USA, 89:5547-5551 (1992)), metallothionein IIA promoter, ecdysone-responsive promoter, and heat shock promoters. Each of these inducible promoters has an inducer or family of inducers that can be used to activate the gene. Selection of the appropriate inducible gene and inducer pair is guided by at which stage the induction then withdrawal of inducer is applied. In the practice of the invention where EMT is induced and progenitor cells produced thereby are administered to a subject and maintained in a progenitor cell state for a selected duration, the inducer selected must be compatible with the subject and be administered to be present at sufficient levels at the cell site to maintain the progenitor cell phenotype. Low toxicity and maintenance of high blood and tissue levels is one set of features. Endogenous agonists or antagonists of the administered inducer can be avoided.

By way of example, the method described in Eilers et al., 1989, Nature 340:66-68, can be used to prepare an inducible transcription factor comprising, for example, the hormone-binding domain of the estrogen receptor and a transcription factor the expression of which induces EMT.

Methods for introducing vectors and other nucleic acids as described above are well known to those skilled in the art, and may include, in some embodiments, the use of lipid or liposome based delivery (WO 96/18372; WO 93/24640; Mannino and Gould-Fogerite (1988) BioTechniques 6(7): 682-691; Rose U.S. Pat. No. 5,279,833; WO 91/06309; and Feigner et al. (1987) Proc. Natl. Acad. Sci. USA 84: 7413-7414) or the use of replication-defective retroviral vectors comprising a nucleic acid sequence as described (see, e.g., Miller et al. (1990) Mol. Cell. Biol. 10:4239 (1990); Kolberg (1992) J. NIH Res. 4: 43, and Cometta et al. (1991) Hum. Gene Ther. 2: 215) Anderson, Science (1992) 256: 808-813; Nabel and Feigner (1993) TIBTECH 11: 211-217; Mitani and Caskey (1993) TIBTECH 11: 162-166; Mulligan (1993) Science, 926-932; Dillon (1993) TIBTECH 11: 167-175; Miller (1992) Nature 357: 455-460; Van Brunt (1988) Biotechnology 6(10): 11491154; Vigne (1995) Restorative Neurology and Neuroscience 8: 35-36; Kremer and Perricaudet (1995) British Medical Bulletin 51(1) 31-44; Haddada et al. (1995) in Current Topics in Microbiology and Immunology, Doerfler and Bohm (eds) Springer-Verlag, Heidelberg Germany; and Yu et al., (1994) Gene Therapy, 1: 13-26. As noted above, in one embodiment, the method described by Elenbaas et al., 2001, Human breast cancer cells generated by oncogenic transformation of primary mammary epithelial cells, Genes & Development 15:50-65, is used to incorporate a transcription factor gene among those exemplified above into an epithelial cell.

In one embodiment, after propagation in vitro in the presence of the inducer, the progenitor cells are administered systemically to the recipient. The inducer may be an agent as described above, or an inducer of an inducible gene as described above. In another embodiment, propagated progenitor cells and the inducer are also administered for a time sufficient to allow the progenitor cells to propagate and populate desired sites within the body; subsequently, discontinuation of administration of the inducer will result in differentiation of the progenitor cells and assumption of their desired local function. In another embodiment, progenitor cells are administered systemically but the inducer is administered locally to the site where proliferation of progenitor cells is desired before differentiation. Once a sufficient population of administered progenitor cells has populated the site, discontinued local administration of inducer will result in differentiation of the progenitor cells.

As will be further described in the isolation section below, at least one additional gene may be included in the inducible or constitutive vector, in order to provide a means for identifying progenitor cells for isolation. In another embodiment, one or more genes may be introduced, or knocked out, or a combination thereof, to modify the progenitor cells before administration for therapeutic uses. For example, a genetic defect in autologous cells can be corrected before the patient's own progenitor cells are administered; for example, a predisposition to cancer in mammary epithelial cells obtained from the patient. In another example, histoincompatibility of allogeneic can be addressed, as described herein. Insertion of blood glucose responsive regulatory machinery to progenitor cells for differentiation into insulin-producing cells is yet another example. The foregoing examples are merely exemplary and not limiting.

By way of non-limiting example, in the instance where the estrogen receptor or a modified estrogen receptor is used, the inducer is an estrogen receptor modulator such as tamoxifen or an analog thereof, such as 4-hydroxytamoxifen. In one embodiment, a modified estrogen receptor only responsive to tamoxifen or an analog thereof, but not to estrogen, is used.

Progenitor cells generated or induced by the aforementioned methods will express at least one marker characteristic of EMT cells as well as progenitor cells. The progenitor cells generated by the methods described herein exhibit a cell surface marker expression pattern characteristic of progenitor cells such as $CD44^{high}$ and $CD24^{low}$. They may also express progenitor cell marker $CD10^{pos}$. The progenitor cells can also exhibit at least one marker of epithelial-mesenchymal transition, from among $FOXC2^{low}$, N-cadherin$^{high}$, E-cadherin$^{low/neg}$, alpha-catenin$^{low/neg}$, gamma-catenin$^{low/neg}$, vimentin$^{pos}$, or fibronectin$^{pos}$. Moreover, the progenitor cells of the invention have multi-lineage potential.

The aforementioned marker profile or expression pattern is readily ascertainable. Marker patterns of cells can be readily determined by techniques, such as cell fluorescence-activated cell sorting and immunohistochemistry to name a few non-limiting examples. As pertains to the foregoing markers and their expression levels, "neg" refers to the absence or negligible level of expression of the marker, and "pos" refers to robust expression. A transition of expression of a cellular marker from "neg" to "pos" represent a change from the lack of expression or low levels of expression to a high level or much higher level of expression. The terms "low" refers to a low level, "high" refers to an easily detectable and high level of expression, and in this case, the transition from low to high expression levels, or from high to low expression levels, is readily apparent to the practitioner. For example, epithelial cells are $CD44^{low}$ and $CD24^{high}$, but upon EMT, CD44 expression increases and CD24 expression decreases, the resulting phenotype being $CD44^{high}$ and $CD24^{low}$. This transition is readily apparent upon cell sorting, for example, as shown in the figures herein, when CD24 expression level is shown on the x-axis and CD44 level on the Y axis; epithelial cells undergoing EMT change in pattern from the lower right quadrant to the upper left as they express progenitor cell characteristics.

3. Isolating progenitor cells generated in the preceding steps. Once EMT has been induced in the desired population of epithelial cells, the progenitor cells are optionally isolated prior to the intended use, be it cell-based therapy, in vitro drug screening or studies on progenitor cells themselves, to name several non-limiting uses. It is not necessary to isolate the progenitor cells from the population of epithelial cells so treated as described above to induce EMT, but may be desirable to enrich or concentrate the population depending on the subsequent use.

Numerous methods exist for isolated such cells, from cell sorting based on the expression of cell-surface progenitor cell markers, selective binding to and/or selective elution from affinity matrices and resins bearing specific binding reagents for expressed markers of the cells desired to be separated. Such binding reagents may be antibodies, lectins, ligands, etc.

Cell sorting can be carried out to isolate a population of desired progenitor cells based on the expression of cell markers, such as those described herein.

Selective binding and/or elution to and from a matrix may be carried out, such as using beads, fibers, and the like. Lectins, antibodies or other binding agents that specifically bind cell surface antigens on the desired cells can be employed; after binding and washing, the desired cells can be eluted. In another embodiment, cells not expressing the progenitor phenotype can be depleted from a population of cells by exposure to a matrix comprising a binding reagent to which the non-progenitor cells bind.

Selective killing of cells not expressing the desired surface markers can be undertaken using a drug resistance selection marker, following methods well known in the art, for example, using HAT selection in the isolation of hybridoma cells (e.g., Szybalski, W., Szybalska, E. H., 1961. Selective systems for measuring forward and reverse mutation rates involving loss and gain of enzyme in human cell lines. V International Congress of Biochemistry. Abstracts and Communications. Moscow, 10-16 Aug. 1961. Pergamon Press Ltd., Oxford, and Panstwowe Wydawnictwo Naukowe, Warsaw, p. 411; Kohler G, Milstein C., 1975, Continuous cultures of fused cells secreting antibody of predefined specificity, Nature 256:495-7).

As mentioned above, co-transfection of an EMT inducer and selectivity marker can be performed such that the progenitor cells can be readily identified from within the population of treated cells, facilitating isolation.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

EXAMPLE 1

Induction of EMT by TGF-β1 Generated CD44high/CD24low Cells

Mammary epithelial cells obtained from reduction surgery samples were exposed in vitro to 5 ng/ml TGF-β1 for 12 days. During this period, the cells changed growth characteristics from confluent growth to a more scattered, mesenchymal cell appearance (FIG. 1B). Cell sorting showed that this change was associated with increased expression of CD44 while concurrently decreasing expression of CD24, such that the cell population shows a transition from $CD44^{low}$ and $CD24^{high}$, to $CD44^{high}$ and $CD24^{low}$ (FIG. 1A).

EXAMPLE 2

Figure 2:
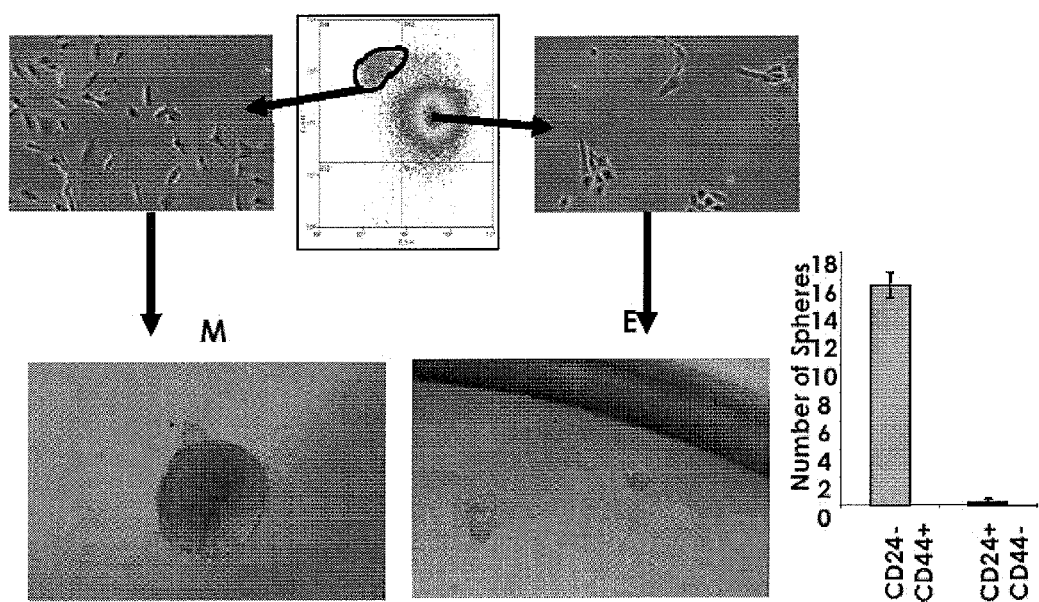
FIG. 2 shows that cells expressing $CD44^{high}$ and $CD24^{low}$ from a human mammary epithelial cell line grow with a typical mesenchymal cell appearance and generate mammospheres in vitro, but cells from the same cell line that express $CD44^{low}$ and $CD24^{high}$ exhibit epithelial cell-like characteristics in culture and do not form mammospheres.

$CD44^{high}$ and $CD24^{low}$ Cells Isolated from Human Mammary Epithelial Cells Form Mammospheres The separate populations of $CD44^{high}$ and $CD24^{low}$, and $CD44^{low}$ and $CD24^{high}$ cells were sorted from a human mammalian epithelial cell line and placed in culture to determine whether mammospheres can form therefrom. The mammosphere culture was performed essentially as described by Wicha et al., 2003, Genes & Development 17:1253-70, with slight modifications. For $CD44^{high}$ and $CD24^{low}$ and $CD44^{low}$ and $CD24^{high}$ human mammary luminal epithelial cells, single cells were plated in ultra-low attachment plates (Corning) at a density of 5000-10,000 cells/mL. Cells were grown in mammary epithelial growth medium (MEGM) from Cambrex (without BPE) supplemented with B27 (Invitrogen), 20 ng/mL EGF and 20 ng/mL bFGF, 4 μg/mL heparin, and 1% methylcellulose. The cells were grown for about 10 days, and the medium changed about every three days. As shown in FIG. 2, left panel, only the $CD44^{high}$ and $CD24^{low}$ cells, which in culture grow with a mesenchymal cell appearance, formed mammospheres, a characteristic of progenitor cells. $CD44^{low}$ and $CD24^{high}$ cells showed epithelial cell like growth characteristics and did not form mammospheres (right panels).

EXAMPLE 3

Only Mesenchymal Cells can give Rise to Mesenchymal Cells and Epithelial Cells

Figure 3:
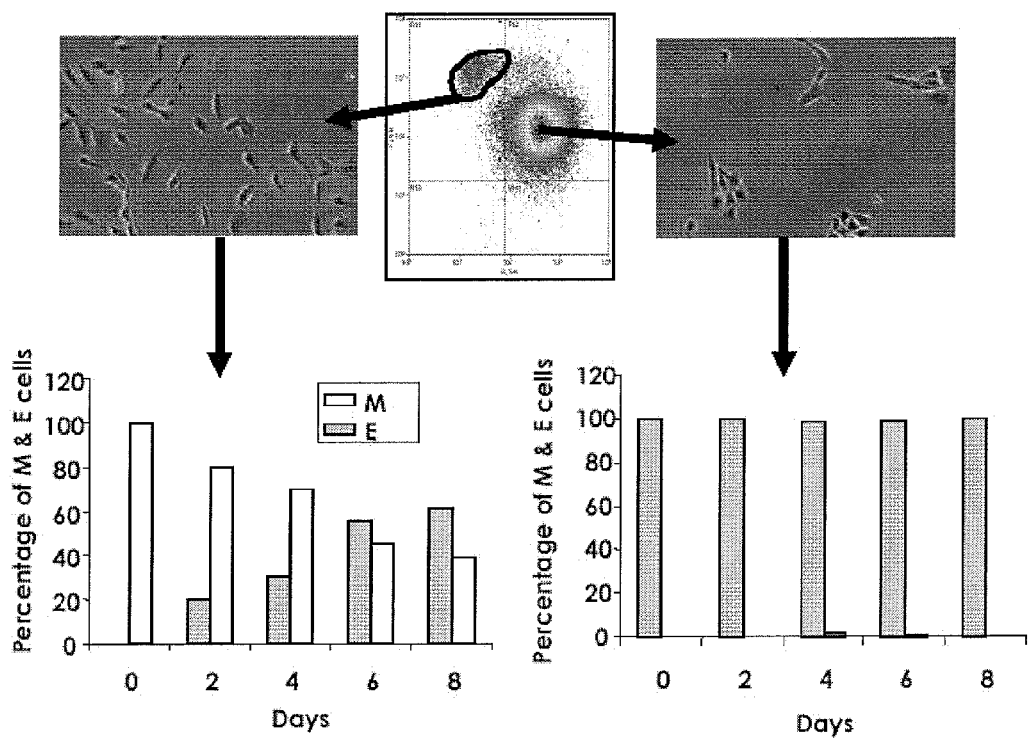
FIG. 3 shows that $CD44^{high}$ and $CD24^{low}$ (progenitor) cells from the human mammary epithelial cell line when placed in culture generate epithelial cells ($CD44^{low}$ and $CD24^{high}$) over time; however, the $CD44^{low}$ and $CD24^{high}$ cells from the cell line remain epithelial-like ($CD44^{low}$ and $CD24^{high}$) and do not generate $CD44^{high}$ and $CD24^{low}$ cells.

Human mammary epithelial cells from a cell line were sorted into $CD44^{high}$ and $CD24^{low}$ cells, and $CD44^{low}$ and $CD24^{high}$ cells, and the expression of these markers was followed over time in culture. As shown in FIG. 3, the $CD44^{high}$ and $CD24^{low}$ (M) cells generated $CD44^{low}$ and $CD24^{high}$ (E) cells and $CD44^{high}$ and $CD24^{low}$ (M) cells over time; however, the $CD44^{low}$ and $CD24^{high}$ (E) cells remained $CD44^{low}$ and $CD24^{high}$ (E) expressing and no $CD44^{high}$ and $CD24^{low}$ (M) cells appeared. Thus, only cells with the phenotype $CD44^{high}$ and $CD24^{low}$ (M) were capable of generating both $CD44^{high}$ and $CD24^{low}$ (M) cells as well as another cell type, $CD44^{low}$ and $CD24^{high}$ (E), identifying the $CD44^{high}$ and $CD24^{low}$ (M) cells as progenitor cells.

EXAMPLE 4

Figure 4:
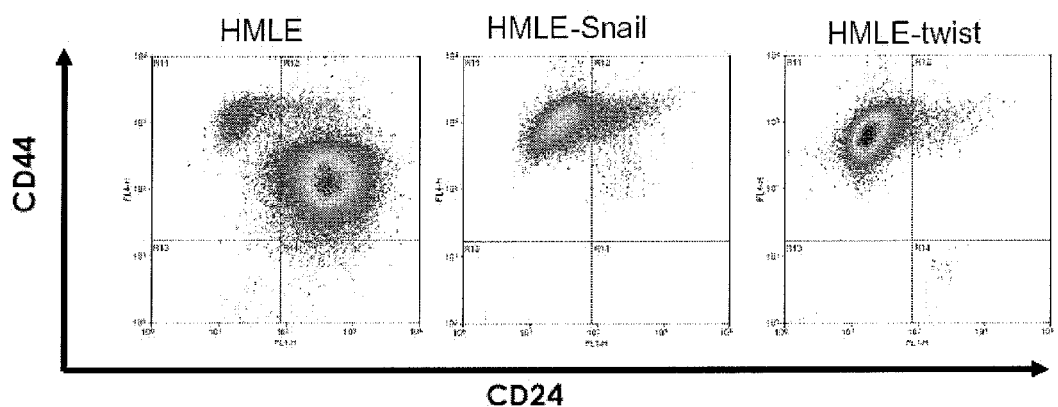
FIG. 4 shows that introducing into human epithelial cells a vector that comprises the transcription factor gene Snail (HMLE-Snail) or Twist (HMLE-Twist) under constitutive control also induces epithelial-mesenchymal transition and results in a population of cells exhibiting a progenitor cell marker pattern of $CD44^{high}$ and $CD24^{low}$ (FIG. 4A), typical growth characteristics (FIG. 4B), as well as progenitor cell marker $CD10^{pos}$ (FIG. 4C)
Figure 4:
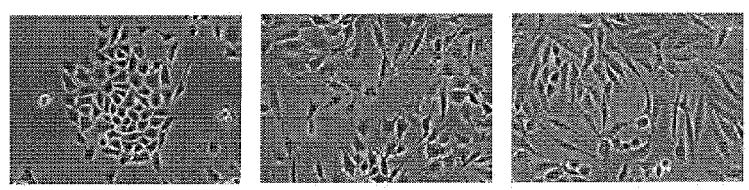
Figure 4:
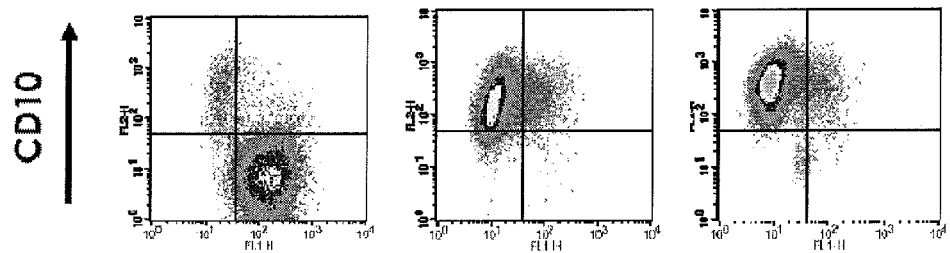

Induction of EMT by Snail or Twist Results in Expression of a $CD44^{high}$ and $CD24^{low}$ Human mammary epithelial cells were transfected with a vector comprising Snail (HMLE-Snail) or Twist (HMLE-Twist) under the control of a constitutive promoter, or vector alone (HMLE). Methods were used generally following those described in Elenbaas et al., 2001, Genes & Development 15:50-65. Preparation of the vectors was as described in Yang et al., 2004, Cell 117:927-937. After transfection with vector alone, the growth of the cells remained confluent. However, cells transfected with a vector comprising the Snail or Twist gene appeared scattered and had a mesenchymal cell appearance (FIG. 4B). Marker analysis showed that while only a very small number of the vector alone-transfected cells (HMLE) expressed the $CD44^{high}$ and $CD24^{low}$ phenotype, all of the cells transfected with Snail or Twist were $CD44^{high}$ and $CD24^{low}$ (FIG. 4A).

EXAMPLE 5

Induction of EMT by Snail or Twist Generates Progenitor Cells

The cells in Example 4 were tested for expression of the progenitor cell marker CD10. As shown in FIG. 4C, the Snail and Twist-transfected cells showed increased expression of CD10 (CD10$^{pos}$), whereas the vector alone-transfected cells were mainly CD10$^{neg}$.

EXAMPLE 6

Inducible Induction of EMT

Figure 5:
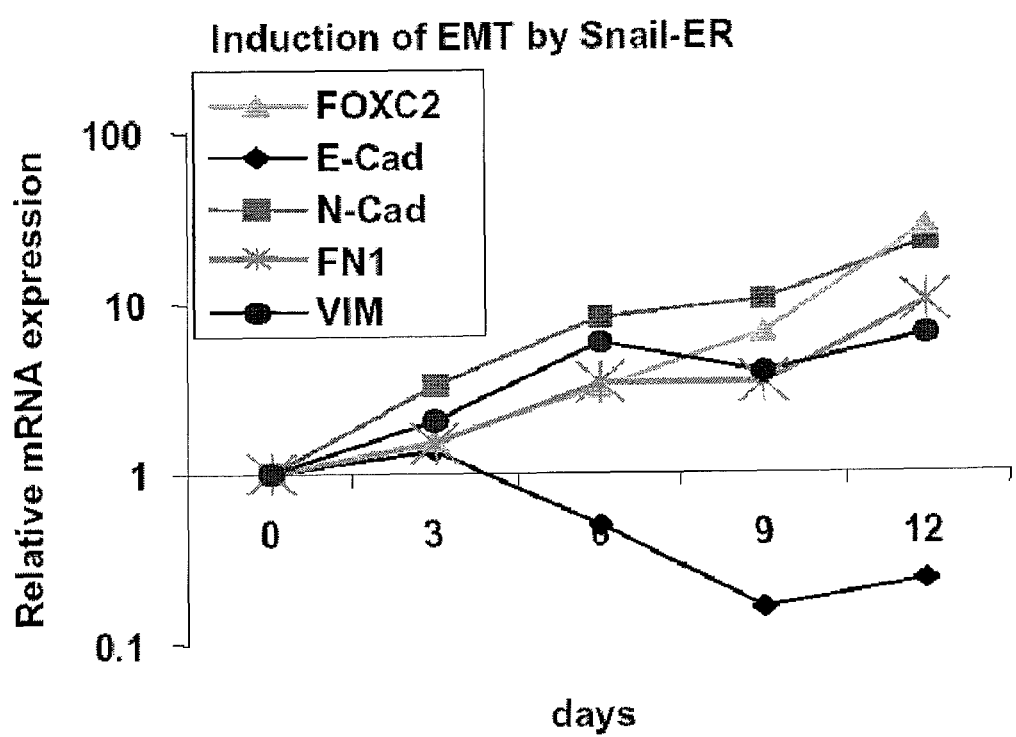
FIG. 5 shows that the introduction of an inducible transcription factor Snail (Snail-ER), and exposure to the inducer tamoxifen results in the appearance over time of mRNA of a marker expression pattern typical of progenitor cells and of epithelial-mesenchymal transition.

Transfection of human mammary epithelial cells with an inducible Snail or Twist-containing vector comprising an transcription factor, Snail or Twist, upon exposure to tamoxifen, produce mammospheres in vitro, and also show increasing expression of the EMT markers FOXC2, N-cadherin, fibronectin and vimentin, while showing a concomitant decrease in the expression of E-cadherin (FIG. 5). The gene containing an inducible transcription factor was prepared following the methods of Eilers et al., 1989, Nature 340:66-68. After 12 days in cell culture in the presence of tamoxifen, cells with inducible Twist construct or an inducible Snail construct transition from an initial CD44$^{low}$ and CD24$^{high}$ phenotype to a CD44$^{high}$ and CD24$^{low}$ phenotype, demonstrating the controlled induction of EMT and appearance of progenitor cell characteristics.

EXAMPLE 7

Figure 6:
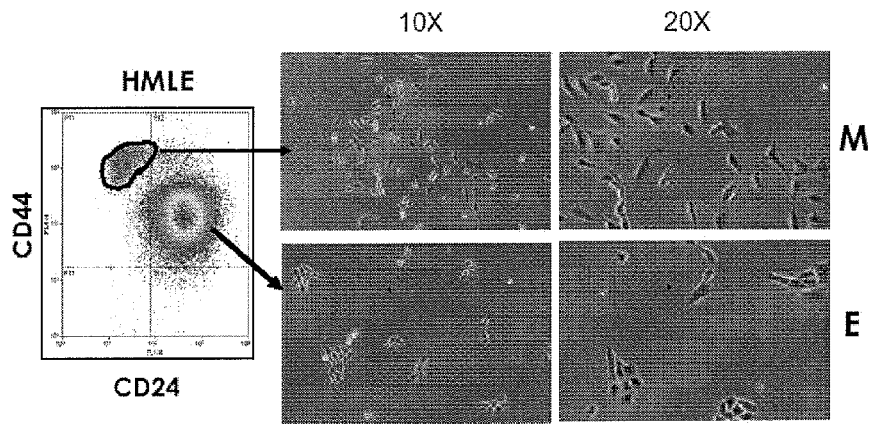
FIG. 6 shows that human mammary epithelial cells isolated from breast reduction surgical tissue contain a subpopulation of cells exhibiting typical growth characteristics of cells having undergone epithelial-mesenchymal transition (FIG. 6A) and a pattern of cell marker expression typical of progenitor cells and of epithelial-mesenchymal transition (FIG. 6B)
Figure 6:
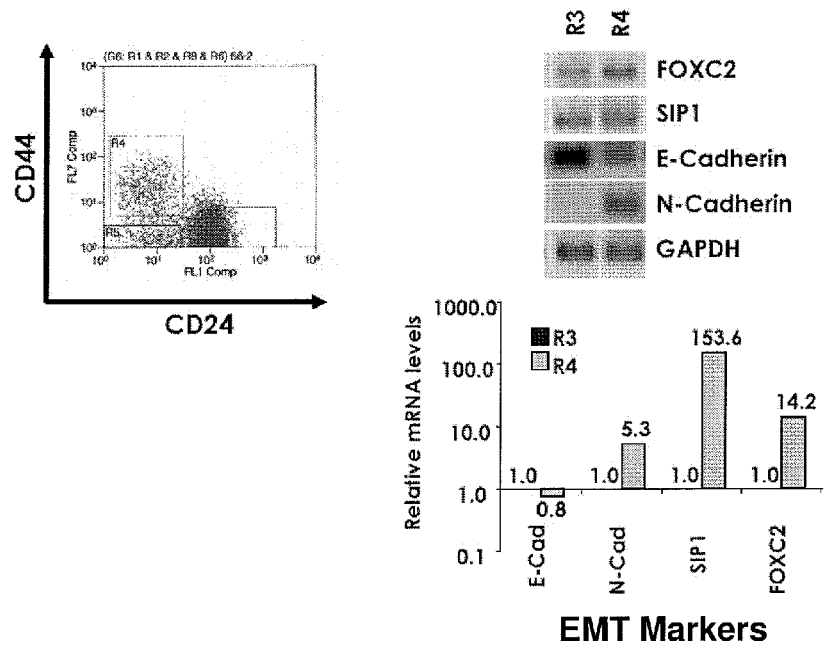

CD44$^{high}$ and CD24$^{low}$ Cells from Human Mammary Epithelial Cells have undergone EMT Human mammary epithelial cells isolated from tissue from breast reduction surgery patients were placed in culture and evaluated microscopically as well as for expression of markers. As shown in FIG. 6A, a small population of these cells expressed the CD44$^{high}$ and CD24$^{low}$ phenotype, and these cells appeared scattered and mesenchymal-like in culture, whereas the bulk of the epithelial cells were CD44$^{low}$ and CD24$^{high}$, and appeared epithelial like in culture.

EXAMPLE 8

Normal Human Mammalian Progenitor Cells Express EMT Markers.

The same two populations from Example 6 were analyzed for the expression of EMT markers E-cadherin, N-cadherin, SIP1, and FOXC2. As shown in FIG. 6B, the CD44$^{high}$ and CD24$^{low}$ low cells expressed higher levels of N-cadherin, FOXC2, and SIP1, and lower levels of E-cadherin, indicative of their EMT phenotype. The CD44$^{low}$ and CD24$^{high}$ cells, in contrast, showed a higher expression of E-cadherin, a lower level of N-cadherin, and lower FOXC2, indicative of the epithelial phenotype.

EXAMPLE 9

Figure 7:
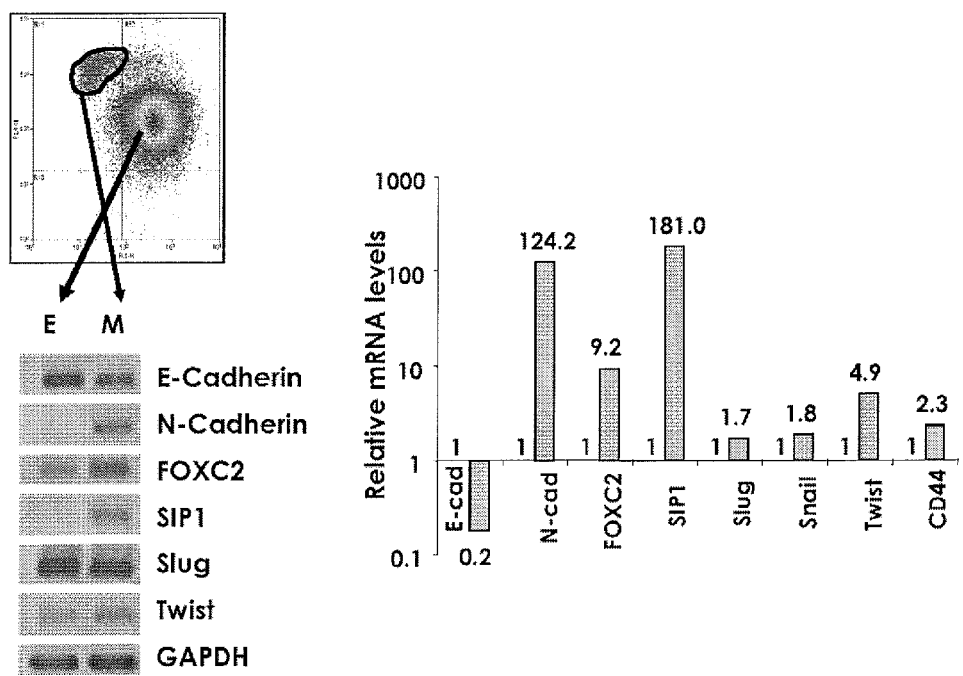
FIG. 7 shows that $CD44^{high}$ and $CD24^{low}$ cells (M) isolated from a human mammary epithelial cell line express markers of epithelial-mesenchymal transition as well as progenitor cell markers, in contrast to $CD44^{low}$ and $CD24^{high}$ cells (E), that do not. Relative mRNA expression values of M cells are shown normalized to E cell values.

CD44$^{high}$ and CD24$^{low}$ Cells Isolated from Human Mammary Epithelial Cell Line Express EMT Markers Cells from a human mammary epithelial cell line were sorted based on levels of CD44 and CD24 expression, and the level of expression of various EMT and progenitor cell markers and other transcription factors were assessed by RT-PCR. The relative mRNA levels of these markers in M cells were expressed relative to the levels in E cells. As shown in FIG. 7, the population of cells that were CD44$^{high}$ and CD24$^{low}$ (M) express markers of epithelial-mesenchymal transition, E-cadherin$^{low/neg}$ and N-cadherin$^{high}$, as well as the progenitor cell marker FOXC2$^{pos}$. CD44$^{high}$ and CD24$^{low}$ cells also expressed elevated levels of transcription factors responsible for inducing EMT: SIP1, Snail, Slug and Twist. In contrast, CD44$^{low}$ and CD24$^{high}$ (E) cells, do not show an expression pattern consistent with those of progenitor cell markers, markers of epithelial-mesenchymal cell transition or transcription factors that induce EMT.

EXAMPLE 10

FOXC2 is a Progenitor Cell Marker

Figure 8:
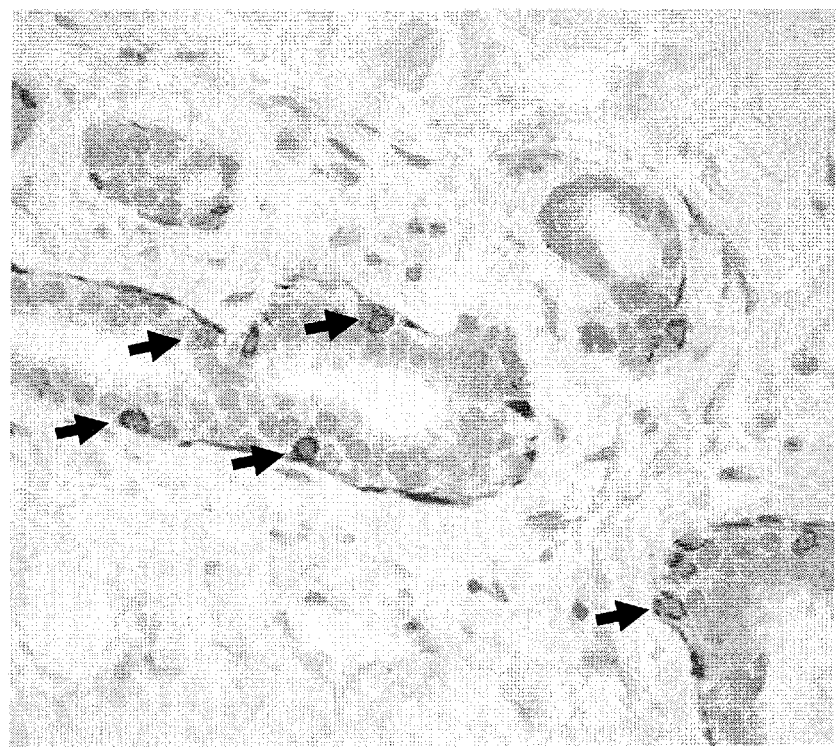
FIG. 8 shows the expression of progenitor cell marker FOXC2 in mammary tissue.

Immunohistochemical staining for FOXC2 in mammary tissue reveals the presence of a small population of cells that express FOXC2 (FIG. 8, arrowheads). As described herein, cells that have undergone EMT and express EMT markers such as N-cadherin$^{high}$, E-cadherin$^{low/neg}$, alpha-catenin$^{low/neg}$, gamma-catenin$^{low/neg}$, vimentin$^{pos}$, or fibronectin$^{pos}$, or any combination of any of the foregoing, also express progenitor cell markers CD44$^{high}$ and CD24$^{low}$, CD10$^{pos}$ as well as FOXC2$^{pos}$. Thus, FOXC2$^{pos}$ is a useful marker of the progenitor cell phenotype.

EXAMPLE 11

Cell-Based Therapy using Induced EMT

Human mammary epithelial cells will be obtained from a patient suffering from chronic heart failure and placed in culture. Transient induction of EMT in the epithelial cells and generation of a population of cells expressing a progenitor phenotype will be achieved by introducing into the epithelial cells a gene encoding an inducible Snail protein, the gene comprising a modified estrogen receptor sensitive to tamoxifen or an analog but not to estrogen. The cells will be maintained in a progenitor state in the presence of tamoxifen. The patient will be placed on tamoxifen therapy and will be administered the progenitor cells as described above. After 4 weekly administrations of cells, tamoxifen therapy will be discontinued. Progenitor cells will populate the heart tissue and differentiate into cardiac muscle and prevent the further deterioration in cardiac function.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method for preparing isolated progenitor cells from epithelial cells comprising the steps of
   a. obtaining a population of primary epithelial cells;
   b. inducing epithelial-mesenchymal transition (EMT) in the population of epithelial cells, whereby CD44$^{high}$/CD24$^{low}$progenitor cells are generated in the population; and
   c. isolating the CD44$^{high}$/CD24$^{low}$ progenitor cells from the population after inducing EMT, wherein said inducing is a method selected from
      i. exposing the population of epithelial cells to an agent that induces epithelial-esenchymal transition;
      ii. introducing into the population of epithelial cells at least one gene encoding a protein that induces epithelial-mesenchymal transition; and iii. the steps of
   a. introducing into the epithelial cells a gene associated with an inducible promoter that encodes a protein that induces epithelial-mesenchymal transition, and
   b. exposing the epithelial cells to an inducer of the expression of the gene.

2. The method of claim 1 wherein said agent is TGF-β1, FGF-1, EGF, HGF/SF, BFGF, or PDGF.

3. The method of claim 1 wherein said gene encoding a protein that induces epithelial-mesenchymal transition is a transcription factor.

4. The method of claim 3 wherein the transcription factor is Snail, Twist, Slug, SIP1, FOXC1, FOXC2, Goosecoid, E47, or a functional variant thereof.

5. The method of claim 1 wherein said gene associated with an inducible promoter that encodes a protein that induces epithelial-mesenchymal transition encodes a transcription factor.

6. The method of claim 5 wherein the gene associated with an inducible promoter encodes a fusion polypeptide comprising the hormone-binding domain of an estrogen receptor.

7. The method of claim 1 wherein the progenitor cells are $FOXC2^{pos}$ or $CD10^{pos}$.

8. A method for inducing the differentiation of progenitor cells comprising the steps of
   a. generating progenitor cells in accordance with claim 1 wherein said inducing comprises introducing into the epithelial cells a gene associated with an inducible promoter that encodes a protein that induces epithelial-mesenchymal transition,
   b. exposing the epithelial cells to an inducer of the expression of the gene; and
   c. withdrawing the inducer.

9. The method of claim 1, further comprising the step of differentiating the isolated progenitor cells in vitro.

10. The method of claim 9, further comprising transplanting the differentiated progenitor cells into a mammalian subject.

11. The method of claim 1 wherein the epithelial cells are from mammary tissue, prostate, lung, keratinocytes, alveoli of the lungs, kidney, small intestine, bladder, ureter or submandibular gland.

12. The method of claim 11 wherein the epithelial cells are from mammary tissue.

13. The method of claim 1 wherein the epithelial cells are squamous epithelial cells, cuboidal epithelial cells, columnar epithelial cells, or transitional epithelial cells.

14. A method for preparing isolated progenitor cells from human mammary epithelial cells comprising the steps of
   a. obtaining a population of primary human mammary epithelial cells;
   b. inducing epithelial-mesenchymal transition (EMT) in the population of human mammary epithelial cells, whereby $CD44^{high}/CD24^{low}$ progenitor cells are generated in the population; and
   c. isolating progenitor cells from the population after inducing EMT, wherein said inducing is a method selected from
      i. exposing the population of epithelial cells to an agent that induces epithelial-mesenchymal transition;
      ii. introducing into the population of epithelial cells at least one gene encoding a protein that induces epithelial-mesenchymal transition; and
      iii. the steps of
         a. introducing into the epithelial cells a gene associated with an inducible promoter that encodes a protein that induces epithelial-mesenchymal transition, and
         b. exposing the epithelial cells to an inducer of the expression of the gene.

15. The method of claim 14 wherein the progenitor cells have multi-lineage potential.

16. The method of claim 14 wherein said agent is TGF-β1, FGF-1, EGF, HGF/SF, BFGF, or PDGF.

17. The method of claim 14 wherein said gene encoding a protein that induces epithelial-mesenchymal transition is a transcription factor.

18. The method of claim 17 wherein the transcription factor is Snail, Twist, Slug, SIP1, FOXC1, FOXC2, Goosecoid, E47, or a functional variant thereof.

19. The method of claim 14 wherein said gene associated with an inducible promoter that encodes a protein that induces epithelial-mesenchymal transition encodes a transcription factor.

20. The method of claim 19 wherein the transcription factor is Snail, Twist, Slug, SIP1, FOXC1, FOXC2, Goosecoid, E47, or a functional variant thereof.

21. The method of claim 14 wherein the gene associated with an inducible promoter encodes a fusion polypeptide comprising the hormone-binding domain of an estrogen receptor.

22. The method of claim 14 wherein the inducer is tamoxifen.

23. The method of claim 14 wherein the progenitor cells are $FOXC2^{pos}$ or $CD10^{pos}$.

24. A method for inducing the differentiation of progenitor cells comprising the steps of
   a. generating progenitor cells in accordance with claim 14 wherein said inducing comprises introducing into the epithelial cells a gene associated with an inducible promoter that encodes a protein that induces epithelial-mesenchymal transition,
   b. exposing the epithelial cells to an inducer of the expression of the gene; and
   c. withdrawing the inducer.

25. A method for inducing the differentiation of progenitor cells at a target site in vivo comprising the steps of
   a. generating progenitor cells in accordance with claim 14 wherein said inducing comprises introducing into the epithelial cells a gene associated with an inducible promoter that encodes a protein that induces epithelial-mesenchymal transition;
   b. introducing the progenitor cells in vivo and administering the inducer in vivo;
   c. waiting a period of time sufficient for the progenitor cells to populate a target site in vivo; and
   d. discontinuing administration of the inducer.

26. The method of claim 14, further comprising the step of differentiating the isolated progenitor cells in vitro.

27. The method of claim 26, further comprising transplanting the differentiated progenitor cells into a mammalian subject.

* * * * *